United States Patent
Appavoo et al.

(10) Patent No.: US 11,857,655 B2
(45) Date of Patent: Jan. 2, 2024

(54) ANTIMICROBIAL COMPOSITIONS COMPRISING MODIFIED CLAY AND NONIONIC TRIBLOCK COPOLYMERS

(71) Applicant: Conopco, Inc., Englewood Cliffs, NJ (US)

(72) Inventors: Shanthi Appavoo, Bangalore (IN); Anindya Dasgupta, Bangalore (IN); Srikala Kumaran, Bangalore (IN); Maya Treesa Saji, Bangalore (IN)

(73) Assignee: Conopco. Inc., Englewood Cliffs, NJ (US)

( * ) Notice: Subject to any disclaimer, the term of this patent is extended or adjusted under 35 U.S.C. 154(b) by 197 days.

(21) Appl. No.: 17/414,270

(22) PCT Filed: Nov. 25, 2019

(86) PCT No.: PCT/EP2019/082364
§ 371 (c)(1),
(2) Date: Jun. 15, 2021

(87) PCT Pub. No.: WO2020/126317
PCT Pub. Date: Jun. 25, 2020

(65) Prior Publication Data
US 2022/0040066 A1    Feb. 10, 2022

(30) Foreign Application Priority Data

Dec. 21, 2018 (EP) ..................................... 18215295

(51) Int. Cl.
| | | |
|---|---|---|
| *A61K 8/25* | (2006.01) | |
| *A61K 8/41* | (2006.01) | |
| *A61K 8/86* | (2006.01) | |
| *A61Q 11/00* | (2006.01) | |

(52) U.S. Cl.
CPC ................. *A61K 8/25* (2013.01); *A61K 8/416* (2013.01); *A61K 8/86* (2013.01); *A61Q 11/00* (2013.01)

(58) Field of Classification Search
CPC ......... A61K 8/25; A61K 8/0256; A61K 8/416
USPC .......................................... 424/49, 401, 404
IPC ....................................................... A61Q 11/00
See application file for complete search history.

(56) References Cited

U.S. PATENT DOCUMENTS

| | | |
|---|---|---|
| 2003/0176537 A1 | 9/2003 | Chaiko |
| 2005/0169852 A1 | 8/2005 | Roberge |
| 2006/0140885 A1 | 6/2006 | Gaffar |
| 2010/0003210 A1 | 1/2010 | Ohara et al. |
| 2012/0171128 A1 | 7/2012 | Ramirez |
| 2012/0177712 A1* | 7/2012 | Bhattacharya ....... A61K 8/0258 564/291 |
| 2012/0251464 A1 | 10/2012 | Subramanyam et al. |
| 2013/0272971 A1 | 10/2013 | Pimenta et al. |
| 2014/0242004 A1 | 8/2014 | Queiroz |
| 2014/0314688 A1 | 10/2014 | Fei et al. |
| 2014/0356299 A1 | 12/2014 | Fei et al. |
| 2015/0157542 A1 | 6/2015 | Schaeffer-Korbylo et al. |
| 2015/0164778 A1 | 6/2015 | Obias et al. |
| 2018/0043190 A1 | 2/2018 | Myers et al. |
| 2018/0112068 A1 | 4/2018 | Segal et al. |

FOREIGN PATENT DOCUMENTS

| | | |
|---|---|---|
| CN | 104869976 | 8/2015 |
| CN | 106924120 | 7/2017 |
| CN | 108430436 | 8/2018 |
| EP | 0288420 | 10/1988 |
| JP | 2004217501 | 8/2004 |
| JP | 2018193500 | 12/2018 |
| WO | WO0207691 | 1/2002 |
| WO | WO03053897 | 7/2003 |
| WO | WO07067340 | 6/2007 |
| WO | WO2007064519 | 6/2007 |
| WO | WO07117498 | 10/2007 |
| WO | WO2011036031 | 3/2011 |
| WO | WO2014102032 | 7/2014 |
| WO | WO2017106763 | 6/2017 |
| WO | WO2019034387 | 2/2019 |
| WO | WO2020126351 | 6/2020 |

OTHER PUBLICATIONS

Search Report and Written Opinion in EP18215295; dated May 21, 2019.
Search Report and Written Opinion in PCTEP2019082364; dated Mar. 30, 2020.
Y.H. Guan et al.; Selection of oral microbial adhesion antagonists using biotinylated *Streptococcus sanguis* and a human mixed oral microflora; Archives of Oral Biology; Aug. 29, 2000; 129-138; 46; www.elsevier.com.
Nik Ahmad Nizam Nik Malek et al.; Characterization and antibacterial activity of cetylpyridinium bromide (CPB) immobilized on kaolinite with different CPB loadings; Applied Clay Science; Jan. 21, 2015; 8-14; 109-110.
Cubells et al.; The effect of a Triclosan/copolymer/fluoride dentifrice on plaque formation and gingivitis: a six-month clinical study; J Clin Dent; 1991; pp. 63-69; English Abstract only; vol. 2(3).
Smith et al.; Use of Pharmacological Agents in Dentifrices for the Prevention of Periodontal Disease; Rev Clin Periodoncia Implantol Rehabil Oral; Nov. 2008; pp. 101-103; English Abstract only; vol. 1(3).

\* cited by examiner

*Primary Examiner* — Walter E Webb
(74) *Attorney, Agent, or Firm* — GREENBERG TRAURIG, LLP

(57) ABSTRACT

The present invention is in the field of antimicrobial compositions, e.g. for personal care. In particular, the invention relates to antimicrobial compositions for oral care, such as toothpastes, comprising antimicrobial particles and a nonionic triblock copolymer. Accordingly, the present invention relates to antimicrobial compositions comprising a modified clay particle, the particle comprising an antimicrobial compound and a clay particle, and at least one a nonionic triblock copolymer. The invention further relates to the uses and methods of the antimicrobial compositions of the invention.

14 Claims, No Drawings

ANTIMICROBIAL COMPOSITIONS COMPRISING MODIFIED CLAY AND NONIONIC TRIBLOCK COPOLYMERS

RELATED APPLICATIONS

The present application is a national phase filing under 35 USC 371 of International Application No. PCT/EP2019/082364, filed on Nov. 25, 2019, which claims priority from European Patent Application No. 18215295.9, filed on Dec. 21, 2018, the contents of which are incorporated herein in their entirety for all purposes.

The present invention is in the field of personal care. In particular, the invention relates to antimicrobial composition that can be used, for instance, in oral care. The antimicrobial compositions comprise modified clay and copolymers. The invention further relates to uses of the antimicrobial composition.

BACKGROUND

Hygiene and appropriate personal care can prevent and treat a number of diseases caused by micro-organisms. An useful instrument to facilitate and improve hygiene includes personal care compositions. The most effective personal care compositions serving this purpose include antimicrobial components that can decrease the microbial count on skin and mucosa surfaces. For instance, antimicrobial compositions in deodorants reduce or prevent the growth of micro-organisms that generate malodor or that promote the decomposition of body oils into odiferous fatty acids. Similar principles apply to shampoos, shower gels, tooth pastes, hand and body washes and other examples of personal care compositions comprising antimicrobial compositions.

The antimicrobial activity of such personal care products ensure not only a cosmetic effect but also can be an effective protection and treatment of a number of diseases and conditions affecting the skin and other body surfaces, such as acne and skin infections (e.g. eczema).

One of the most important aspects of personal care is oral health. Cavities, tartar, gum diseases e.g. gingivitis, plaque and halitosis are diseases (or conditions resulting from or that may lead to diseases) in the oral cavity that can be easily prevented or treated by adequate oral hygiene. These diseases and conditions are not only of importance from a medical perspective but also from the cosmetic point of view as they may impair one's smile appearance (such as teeth yellowing or bad breath, that not necessarily has a pathological origin). In any case, an unhealthy and/or impaired oral condition may affect people's social activities, sometimes resulting in reclusion, anxiety, depression or panic. As much as it is relevant for the oral health of human subjects, oral care is also of increasing importance in the veterinary industry, either for pets or large animals.

Oral diseases and cosmetically impairing oral conditions develop from the formation of biofilm on the surface of teeth. Oral biofilm affects the cosmetic appearance for it facilitates teeth discoloration and/or staining. Also, oral biofilm allows microorganisms attachment to the teeth surface possibly resulting in diseases.

Oral biofilm is formed by attachment of acquired pellicle, which is a thin protein-containing film derived from salivary glycoproteins, to a clean tooth surface. The pellicle allows bacteria adhesion from so-called pioneer species, such as *Actinomyces* spp, *Streptococcus* spp, *Haemophilus* spp, *Capnocytophaga* spp, *Veillonella* spp, and *Neisseria*, to the tooth surface. This early stage of biofilm formation can be easily reversed. However, if not removed, the pioneer bacteria will enable the subsequent attachment of bacterial species such as *Fusobacterium nucleatum*, *Treponema* spp, *Tannerella forsythensis*, *P. gingivalis*, *Aggregatibacter actinomycetemcomitans*, etc., that are related to the formation of plaque, tartar, gum diseases, etc.

Halitosis may be a symptom of oral diseases as it often indicates the presence of pathogens causing e.g. cavities and gingivitis. However, halitosis is not always connected to a medical condition. Bad breath, or mouth malodor, may be caused, for instance, by some medicaments, excessive caffeine consumption or reduced saliva production (dry mouth). When non pathological, halitosis can be prevented or controlled with oral care compositions, such as mouthwashes, chewing gums, toothpastes, breath tablets, and other products that ensure oral cleaning and provide a fresh breath.

US2012/0171128A1 describes an oral cleaning composition. In the examples, it is described a cleaning system comprising first composition and a second composition that are co-dispensed or sequentially dispensed. The first composition is a viscous gel comprising 88 wt. % water, poloxamer 407 5.0 wt. %, hydrogen peroxide at 3 wt. %, glycerin at 3 wt. %, and a sufficient amount to make a total of 100 wt. % of phosphoric acid/water. The second composition comprises 32 wt. % lemon peel dust and 67 wt. % glycerine, water/sodium hydroxide solution in a rinse or gel form.

EP0288420A1 describes aqueous hydrogen peroxide dental gel compositions comprising 18-25 wt. % polyethylene polypropylene block copolymer (Pluronics) as gelling agent, polyethylene glycol, sodium saccharin, nonionic surfactant and flavor.

WO 2011/036031 A1 describes a bipolar antimicrobial particle for use in laundry detergent compositions, fabric conditioners, personal care and cosmetic compositions and a process for making the same. The antimicrobial particle described therein comprises a modified clay particle with an antimicrobial group attached thereto. The examples describe the preparation of the modified clay particles and its antimicrobial activity, in particular on fabrics.

There remains a need for antimicrobial compositions with further improved antimicrobial activity, in particular for use in personal care antimicrobial compositions such as compositions for oral care.

SUMMARY OF THE INVENTION

The present inventors have surprisingly found that modified clay particles comprising antimicrobial components present an improved antimicrobial activity when used in a composition further comprising a nonionic triblock copolymer.

Accordingly, in a first aspect, the invention relates to an antimicrobial composition comprising:
  a) a modified clay particle comprising an antimicrobial compound, the modified clay particle comprising:
    (i) an asymmetric 1:1 or 2:1:1 clay particle comprising alternating tetrahedral and octahedral sheets terminating with a tetrahedral sheet at one external surface plane and an octahedral sheet at another external surface plane, and
    (ii) at least one orally acceptable antimicrobial compound selected from a quaternary ammonium material selected from cetylpyridinium chloride (CPC), cetyltrimethylammonium chloride (CTAC), cetyltrimethylammonium bromide (CTAB), benzalkonium chloride (BKC), benzethonium chloride, cetrimide, quaternium, polyhexamethylene BH;

antimicrobial alcohols; antimicrobial phenols; antimicrobial organic acids/salts; zinc pyrithione; ketoconazole; piroctone olamine; or combinations thereof, wherein the at least one antimicrobial compound is attached to the coordinating cation on an external surface plane of the clay particle; and b) a nonionic triblock copolymer.

In a second aspect, the antimicrobial composition according to the invention is for use in the prevention or treatment of a disease of a mammal.

In a third aspect, the antimicrobial composition of the invention is for use in the removal of oral biofilm in a mammal subject.

In a fourth aspect, the invention relates to a non-therapeutic method of treating the skin or oral cavity of a mammal, the method including the step of contacting the skin or oral cavity of a mammal with the antimicrobial composition according to the present invention.

In yet another aspect, the invention relates to the use of an antimicrobial composition of the invention for reducing body malodor, preferably mouth malodor, and/or for reducing oral biofilm formation and/or for reducing tooth discoloration, in a mammal.

DETAILED DESCRIPTION OF THE INVENTION

Antimicrobial Particle

The composition according to the invention comprises a modified clay particle comprising an antimicrobial compound, the modified clay particle comprising an asymmetric 1:1 or 2:1:1 clay particle having alternating tetrahedral and an octahedral sheets terminating with a tetrahedral and an octahedral sheet at exterior surface planes. Particle of 1:1 clay is preferred.

The particle is prepared from a precursor with bipolar topospecific characteristics. Any chemical reaction or series of reactions wherein an antimicrobial compound is attached selectively to coordinating cations on the exterior plane of either the tetrahedral or the octahedral surface plane of asymmetric clay can be used to prepare the bipolar particle comprising an antimicrobial compound used in the present invention. In order to obtain a true bipolar antimicrobial particle it is preferred that the reaction is selective to only one of the exterior planes. By selective is meant that more than 50% of the total antimicrobial compound is present on one of the exterior planes, preferably more than 75%, more preferably than 80%, still more preferably than 90%, even more preferably than 95%, or even more than 99%. The bipolar particle comprising an antimicrobial compound used in the composition according to the invention can be prepared, e.g. by the process described in WO 2011/036031, incorporated herein by reference.

According to the present invention, preferred 1:1 clays include kaolinite and serpentine subgroups of minerals. The species included within the kaolinite subgroup include but are not limited to kaolinite, dickite, halloysite and nacrite. The species within the serpentine subgroup include but are not limited to chrysolite, lizardite, and amesite.

According to the present invention, preferred 2:1:1 clays include chlorite group of minerals. Chlorite is sometimes wrongly referred to as 2:2 clay by some mineralogists.

The chlorite comprises tetrahedral-octahedral-tetrahedral sheets like 2:1 clays, with an extra weakly bound brucite like layer between tetrahedral layers.

The tetrahedral sheet preferably comprises coordinating tetrahedral cations of silicon. The tetrahedral sheet may also comprise isomorphously substituted coordinating tetrahedral cations which are not silicon. Isomorphously substituted coordinating tetrahedral cations include, but are not limited to, cations of aluminum, iron or boron.

The octahedral sheet preferably comprises coordinating octahedral cation of aluminum. The octahedral sheet may also comprise isomorphously substituted coordinating octahedral cations which are not aluminium. Isomorphously substituted coordinating octahedral cations include cations of magnesium or iron.

The at least one antimicrobial compound is attached to the coordinating cation on an external surface plane of the clay particle. Preferably, no antimicrobial compound is attached to coordination cations of non-exterior tetrahedral or octahedral plane or on the interior side of the surface sheets.

The antimicrobial compound may be attached to coordinating cations on the exterior side of the tetrahedral sheet or to the coordinating cations on the exterior side of the octahedral sheet. Preferably, the at least one antimicrobial compound is attached to the coordinating cations on the external surface of the octahedral surface plane.

The at least one antimicrobial compound may be attached to coordinating cations on the exterior side of the same surface sheet or on the exterior side of each of the tetrahedral and the octahedral surface sheets. The antimicrobial compounds may be the same or different. Preferably, the antimicrobial compound attached to the coordinating cations on the exterior side of the tetrahedral surface sheet is preferably not identical to the compound attached to the coordinating cations on the exterior side of the octahedral surface sheet.

Preferably, the modified clay particle has a clay:antimicrobial compound ratio is between 1:0.001 and 1:0.1, more preferably between 1:0.01 and 1:0.05, most preferably about 1:0.018.

Antimicrobial Compound

The antimicrobial compound is preferably selected from the group of quaternary ammonium salts, antimicrobial alcohols, antimicrobial phenols, antimicrobial organic acids/salts, or combinations thereof.

Preferred antimicrobial alcohols include, but are not limited to phenoxy ethanol, benzyl alcohol, dichlorobenzyl alcohol, dimethyl oxazolidine, DMDM Hydantoin, 2-bromo-2-nitropropane-1,3-diol, diazolidinyl urea, hexachlorophene.

Preferred antimicrobial phenols include, for instance, triclosan, Thymol, dichlorophenol, 2-chloro-4-fluoro phenol, tetrafluorobenzoic acid, cresol, hexylresorcinol, microlides, etc.

Preferred antimicrobial organic acids/salts are selected from benzoic acid/sodium benzoate, salicylic acid/sodium salicylate, sorbic acid/potassium sorbate, sodium hydroxymethyl glycinate, cyclohexane diacetic acid monoamide, chloronicotinic acids, succinic acid, peracetic acid or zinc pyrithione, ketoconazole, piroctone olamine (Octopirox®), or combinations thereof.

Preferred quaternary ammonium salts are selected from the group comprising cetylpyridinium chloride (CPC), cetyltrimethylammonium chloride (CTAC), cetyltrimethylammonium bromide (CTAB), benzalkonium chloride (BKC), benzethonium chloride (BZC), cetrimide, quaternium, polyhexamethylene BH. Further more preferred quaternary ammonium salts are selected from the group comprising CPC, CTAC, CTAB, BKC, or BZC. By quaterium is meant a compound having a quaternary ammonium group.

In a preferred embodiment, the at least one antimicrobial compound is a quaternary ammonium salt, more preferably the at least one antimicrobial compound is cetylpyridinium chloride (CPC).

The concentration of the antimicrobial compound in the antimicrobial composition will depend on the use of the composition. Accordingly, in some embodiments, the antimicrobial composition will comprise modified clay particles comprising the antimicrobial compound in a therapeutically effective amount. In another embodiments, the antimicrobial composition will comprise modified clay particles comprising the antimicrobial compound in a cosmetically effective amount.

Typically, the composition comprises from 0.001 wt. % to 50 wt. % of the modified particle (La, the particle comprising the at least one antimicrobial compound), by total weight of the composition, more preferably 0.01 wt. % to 20 wt. %, even more preferably from 0.1 wt. % to 10 wt. %, most preferably from 1 wt. % to 5 wt. %, by total weight of the composition, even most preferably 0.2% to 3% by weight of the composition. Preferably, the antimicrobial compound is CPC, thus the particle is a CPC-clay particle, present in the composition in an amount between 0.01 wt. % to 50 wt. %, more preferably between 0.1 wt. % to 20 wt. %, even more preferably between 1 wt. % to 5 wt. %.

Nonionic Triblock Copolymer

Block copolymers are based on ethylene oxide and propylene oxide. Polyoxyethylene polyoxypropylene block copolymers (Poloxamers) are composed of a central hydrophobic chain of polyoxypropylene (poly(propylene oxide)) flanked by two hydrophilic chains of polyoxyethylene (poly (ethylene oxide)). Suitable triblock copolymers are known by the trade names Pluronics, Synperonics and Kolliphor.

Preferably, the polyoxyethylene polyoxypropylene block copolymers is present in an amount of 0.001-20 wt. %, more preferably 0.01-10 wt. %, even more preferably 0.1-10 wt. %, most preferably, 1-5 wt. %, by weight of the antimicrobial composition.

Preferably, the copolymer is selected from Pluronic Polyols which are nonionic and may be represented by the general formula I:

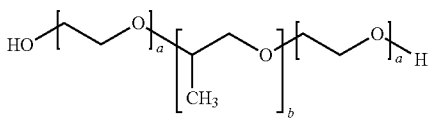

wherein a is an integer such that the hydrophobic base represented by (C3H6O) has a molecular weight of about 2750 to 4000, b is an integer such that the hydrophilic portion (moiety) represented by (C2H4O) 25 constitutes about 70-80% by weight of the copolymer. Pluronic Polyols of the F (solid flake or powder) type, with a hydrophobe of M.W. of about 2750 to 4000 and with from 70 to 80% hydrophilic polyoxyethylene groups form a gel at 18-25% by weight of the H2O2/Pluronic gel formulation.

Examples of suitable Pluronic compounds are Pluronic F88, F98, F108 and F127. The most preferred gelling agent is Pluronic F127, which has a molecular weight of 4000 and contains 70% of the hydrophilic polyoxyethylene moiety.

Preferably, the nonionic triblock copolymer is a poloxamer of general formula I wherein a is 101 and b is 56.

In one embodiment, the composition is an oral care composition. Preferably, the oral care composition is selected from toothpaste, dentifrice (e.g. in gel or powder), tooth powder, topical oral gel, mouth rinse, denture product, mouth spray, lozenge, oral tablet, chewing gum, impregnated dental implement, dental floss, and combinations thereof. Pluronic compounds are preferably employed in oral care compositions according to the invention in an amount of 0.001-20%, more preferably 0.01-10%, even more preferably 0.1 wt. % to 5 wt. %, by weight of the composition. Preferably, these amounts of pluronic are used in a composition comprising a modified particle which is a CPC-clay particle.

Antimicrobial Compositions

The antimicrobial composition according to the invention is preferably an antimicrobial composition for personal care, such as a composition selected from oral care compositions, shampoos, deodorants (optionally comprising propellant), hand- or body-wash, etc.

In one embodiment of the invention, the composition is present in creams (including UV-A and UV-B sunscreens), soaps, gels, deodorants, shampoos or hand- or body-wash compositions. Body-wash compositions are also known as detergent compositions. Deodorants, shampoos or hand- or body-wash compositions may comprise further conventional components, such as surfactants, humectants, fragrance, buffering agents, skin soothing agents, preservatives, UV-A or UV-B sunscreens, etc.

Preferably, the composition comprises solvents such as ethyl alcohol, isopropanol, acetone, ethylene glycol monoethyl ether, diethylene glycol monobutyl ether, diethylene glycol monoethyl ether and mixtures thereof.

The composition may also comprise a non-phenolic alcohol. The non-phenolic alcohol preferably selected from e.g. aliphatic alcohol, monohydric alcohol. The most preferred non-phenolic alcohol is monohydric alcohol. Preferably, the alcohol having straight or branched chain of carbon atoms preferably containing from 1 to 16, more preferably from 2 to 10, even more preferably from 3 to 8 carbon atoms. Illustrative examples of alcohol that may be used in the composition include methyl alcohol, ethyl alcohol, isopropyl alcohol, n-propyl alcohol, isobutyl alcohol, n-butyl alcohol, n-pentyl alcohol, n-hexyl alcohol and mixtures thereof. Preferably, alcohol is selected from ethyl alcohol, isopropyl alcohol and mixtures thereof. Preferably, the composition comprises from 40 to 95%, more preferably from 45 to 90%, even more preferably from 50 to 85%, still more preferably 55 to 80%, yet more preferably from 60 to 75% and most preferably from 65 to 70%, by weight, of a non-phenolic alcohol.

Advantageously, the composition may preferably comprise ingredients like vitamins, anti-acne actives, anti-wrinkle, anti-skin atrophy and skin repair actives, skin barrier repair actives, non-steroidal cosmetic soothing actives, artificial tanning agents and accelerators, sebum stimulators, sebum inhibitors, anti-oxidants, protease inhibitors, skin tightening agents, anti-itch ingredients, hair growth inhibitors, 5-alpha reductase inhibitors, desquamating enzyme enhancers, anti-glycation agents and mixtures thereof.

The composition may preferably comprise powders like e.g. chalk, talc, fillers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate and mixtures thereof.

Preferably, the antimicrobial composition according to the invention further comprises surfactants. Preferably, the surfactants are selected from anionic, nonionic, cationic, amphoteric surfactants and mixtures thereof. More preferably, surfactants are selected from cationic surfactant, nonionic surfactant and mixtures thereof.

Preferred anionic surfactants include soap, alkyl ether sulfate and sulfonates, alkyl sulfates and sulfonates, alkylbenzene sulfonates, alkyl and dialkyl sulfosuccinates, C8-C20 acyl isethionates, acyl glutamates, C8-C20 alkyl ether phosphates and mixtures thereof.

Preferred nonionic surfactants are those with a C10-C20 fatty alcohol or acid hydrophobe condensed with from 2 to 100 moles of ethylene oxide or propylene 30 oxide per mole of hydrophobe; C2-C10 alkyl phenols condensed with from 2 to 20 moles of alkylene oxide; mono- and di-fatty acid esters of ethylene glycol; fatty acid monoglyceride; sorbitan, mono- and di-C8-C20 fatty acids; block copolymers (ethylene oxide/propylene oxide); polyoxyethylene sorbitan and mixtures thereof. Alkyl polyglycosides and saccharide fatty amides (e.g. methyl gluconamides) are also suitable nonionic surfactants.

Preferred cationic surfactant include cetyl trimethylammonium bromide, benzalkonium halides that are also known as alkyldimethylbenzylammonium halides. Preferred cationic surfactant that may be used in the composition is benzalkonium chloride, also known as alkyldimethylbenzylammonium chloride.

Preferred amphoteric surfactant include amide, betaine and amine oxide type. Particularly amphoteric surfactants include cocodiethanol amide and cocomonoethanol amide, cocoamidopropyl betaine and coco amido propyl amine oxide. A preferred amphoteric surfactant that may be used as a surfactant in the composition is cocoamidopropyl betaine.

When incorporated in the composition, surfactants may be present in an amount from 1 to 80%, preferably from 3 to 60%, more preferably from 5 to 40%, even more preferably from 7 to 30%, further more preferably from 9 to 15% by weight of the composition.

Preferably, the composition further comprises a cosmetically or pharmaceutically acceptable base. The cosmetically or pharmaceutically acceptable base is preferably in the form of a cream, lotion, gel or emulsion. Water and/or alcohol may also be used a cosmetically or pharmaceutically acceptable base. Alcohol may be a mono or polyhydric alcohol. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Preferably, the cosmetically or pharmaceutically acceptable base is present preferably from 10 to 99.9%, more preferably from 50 to 99%, even more preferably from 60 to 85% and further more preferably from 65 to 80% by weight of the composition.

In a preferred embodiment, the antimicrobial composition is present in an oral care product. Accordingly, the composition according to the invention is preferably included in an oral care product selected from toothpaste, dentifrice, tooth powder, topical oral gel, mouth rinse, denture product, mouth spray, lozenge, oral tablet, chewing gum, impregnated dental implement, dental floss, and combinations thereof. More preferably, the oral care product is dental care product, such as tooth powder, toothpaste, impregnated dental implement, dental floss.

Preferably, the composition comprises one or more orally acceptable component, such as abrasives, orally accepted actives (such as Fluor), teeth whiteners, fragrances, stabilizers, preservatives, among other conventional components to oral care compositions.

Uses of the Antimicrobial Composition

The present inventors have found that the antimicrobial composition according to the invention has an improved antimicrobial activity. Accordingly, the antimicrobial composition can be used for cosmetic (non-therapeutic) or therapeutic applications.

a) Therapeutic Uses

In one aspect, the antimicrobial composition according to the invention is for use in the prevention or treatment of a disease of a mammal. Diseases as used herein refer to diseases caused by micro-organisms on body surfaces (skin, nails, mucosa, etc.). In one embodiment the diseases are skin diseases such as selected from the group comprising acne, eczema, or bacterial or fungal infections on the scalp, nails or skin, such as those caused by *Propionibacteria* spp., *Corynebacteria* spp., *Actinobacteriales*, *Staphylococci* spp. (e.g. *S. epidermidis*), *Lactobacilales*, *Clostridiales*, *proteobacteria*, *Flavobacteriales*, *Bacteriodales*, *Malassezia* yeasts (e.g. *Malassezia furfur* and *Malassezia globosa*), among others.

Preferably, the use is in the prevention or treatment of a disease in the oral cavity. Preferred diseases in the oral cavity are selected from caries, tartar, dental plaque, gum diseases, and combinations thereof, for instance diseases caused by *Actinomyces* spp, *Streptococcus* spp (such as *S. mutans* and *S. sobrinus*), *Lactobacillus* ssp. (such as, *Lactobacillus acidophilus*), *Nocardia* spp., *Haemophilus* spp, *Capnocytophaga* spp, *Veillonella* spp, *Neisseria*, *Fusobacterium*, such as *F. nucleatum*, *Treponema* spp, *Tannerella* ssp., such as *T. forsythensis*, *P. gingivalis*, *Aggregatibacter actinomycetemcomitans*, and others.

In a further aspect, the antimicrobial composition of the invention is for use in the removal of oral biofilm in a mammal subject.

Typically, the particle comprising an antimicrobial compound is preferably incorporated in the composition for the cosmetic use in an amount from 0.05% to 10% by weight of the composition, more preferably from 0.1% to 10%, most preferably from 0.2% to 5% by weight of the composition. The clay:antimicrobial ratio is between 1:0.001 and 1:0.1, more preferably between 1:0.01 and 1:0.05, most preferably about 1:0.018. Preferably, the antimicrobial composition for the therapeutic uses according to the invention comprises a therapeutically effective amount of an antimicrobial compound.

b) Cosmetic/Non-Therapeutic Uses

The present invention provides cosmetic uses of the antimicrobial composition on body surfaces, such as skin, teeth, scalp, mucosa (gums), tongue, etc. The inventors have found an improved antimicrobial activity on micro-organisms normally found on said body surfaces and that may impair body appearance (such as teeth yellowing) or body odor, in particular mouth malodor. Preferably, the antimicrobial composition is for the cosmetic use in the prevention or treatment of halitosis caused by microorganisms in the oral cavity.

Accordingly, in yet another aspect, the invention relates to a non-therapeutic method of treating the skin or oral cavity of a mammal, the method including the step of contacting the skin or oral cavity of a mammal with the antimicrobial composition according to the present invention.

In another aspect, the invention relates to the use of an antimicrobial composition of the invention for reducing body malodor, preferably mouth malodor, and/or for reducing oral biofilm formation and/or for reducing tooth discoloration, in a mammal.

The particle comprising an antimicrobial compound is preferably incorporated in the composition for the cosmetic use in an amount from 0.05% to 10% by weight of the composition, more preferably from 0.1% to 10%, most preferably from 0.2% to 5% by weight of the composition.

EXAMPLES

Example 1: Preparation of Modified Clay Particle

To prepare the modified clay particle comprising an antimicrobial compound according to the invention, the following method was used:

5 g of Kaolinite (Super shine 90, EICL) was taken in a 500 ml of 0.1N HCl (Merck) solution and sonicated for 30 minutes. The pH is then increased to 9 by addition of NaOH (Merck) solution drop wise. To this 10 g CPC was added and the suspension was stirred over a magnetic stirrer (Spinpot) for 6 hours while maintaining the temperature of the solution at 75-80° C. The suspension was then washed with water for about 10 times to remove the excess CPC and a final ethanol (Les Alcools De Commerce) wash was given. The clay was then dried in a hot air oven.

To determine that CPC was attached on the clay after reaction FTIR-spectroscopy method was utilized. The instrument used was Perkin Elmer instruments, Spectrum One FT-IR Spectrometer. Powder (diffuse reflectance) technique was utilized for this measurement. Clay as control and reacted clay of the invention were grounded with 50% w/w of KBr in a pestle and mortar and then IR was done on these powders. The IR spectrum of the reacted clay was compared against that of pure clay. New peaks were observed in the reacted clay at the wave numbers of 2926 cm-1, 2855 cm-1, 1487 cm-1 and 1466 cm-1. The peaks at 2926 cm-1 and 2855 cm-1 are due to the C—C stretching of the alkyl chain of the CPC, while the peaks at 1487 cm-1 and 1466 cm-1 are due to the ring carbon and nitrogen of the CPC.

Example 2: Antimicrobial Activity of the Actives

Antimicrobial activity of the compositions according to the invention has been compared with compositions comprising either only the modified clay particle comprising an antimicrobial compound ('CPC', prepared as in Ex. 1), or only a nonionic triblock copolymer ('pluronic'). Salivary flora and actives (according to Table 1 below) were co-incubated overnight and at the end of incubation biofilm was stained with crystal violet. Detailed protocol as mentioned below:

Treatment and Biofilm Formation

Early morning saliva samples before brushing was collected from 4-5 people, pooled together and washed twice in saline. Absorbance was set to 0.2 OD620 nm in ultra-filtered tryptone yeast extract broth (2% sucrose) and used for experiments as mentioned in further steps. 2 ml of set culture was added into 24/12 well plate to which test actives at varying concentrations were added into each of the wells. The plate was incubated anaerobically overnight at 37° C.

Staining Protocol

At the end overnight incubation, decant the plate out over a biohazard bag to remove all the planktonic bacteria. Rinse the plate in a tray of water and decant the water out over the tray. This step was done once to remove the loosely adhered biofilm. Place the plate on a blotting paper/paper towel over the bench top. Stain all the test wells with 1 ml of 1% Crystal violet stain (CV) for 10 min. This step was done using a pipette. Decant the plate out over the biohazard discard bag to remove all the stain. Rinse the plate in a tray of water and pour the water out over the tray. This step was done thrice consecutively, in three separate trays of water. (Each tray procedure was repeated thrice-total 9 rinse). Cover the bench top with more blotting paper/paper towel and hit the plate against the bench top until all the wells are free of any liquid. This step was done to ensure that only CV remaining is bound to a biofilm at the bottom of a well. Leave the plate face up on the bench top at room temperature (23+2° C.) until it dries completely. Add 1 ml of 33% glacial acetic acid to the test wells to solubilize the biofilm bound CV stain. Allow the acetic acid to sit for 10 mins. Pipette up and down the mix of acetic acid and CV in the wells.

Transfer 10 μl of above solution mix to 90 ul of 33% acetic acid in a well of flat bottom 96 well plate. Mix the solution well and absorbance is taken at 540 nm. All the test actives were done in duplicates.

TABLE 1

|  | % Biofilm |
| --- | --- |
| Bacterial control | 100 |
| 0.01% CPC-Clay | 83 |
| 0.001% Pluronic | 76 |
| 0.001% Pluronic + 0.01% CPC-Clay | 29 |
| 0.001% Pluronic + 0.005% CPC-Clay | 52 |

Example 3: Antimicrobial Activity of the Actives in Toothpaste Formulations

Antimicrobial activity of the compositions according to the invention has been compared with compositions comprising either only the modified clay particle comprising an antimicrobial compound ('CPC', prepared as in Ex. 1), or only a nonionic triblock copolymer ('pluronic'). The compositions (Table 2) were tested according to the following method.

Pellicle coated HAP disc was treated with toothpaste base formulation topped up with actives for 2 mins, subjected to sterile water wash and challenged with salivary flora and incubated overnight. At the end of incubation, the discs were stained with Plaque disclosing dye (Plak-check, Vishal Dentocare PVT.LTD). The detailed method is as follows:

Early morning saliva was collected from 5-6 volunteers and pooled. The pooled saliva was pelleted by centrifuging at 4000 g for 10 min to produce salivary pellicle (the supernatant was filter sterilized through 0.22 um filter and stored at 4° C.) and salivary flora (pellet was washed twice in 5 ml of 1×PBS (pH7.0) by centrifugation). The salivary flora was adjusted to 108 Log CFU/ml (0.2 OD620 nm) in ultra-filtered Tryptone yeast extract broth (nutrient media) containing 2% sucrose.

Each sterile HAP was coated with salivary pellicle (discs were placed horizontally in 12 well plate) to allow the initial pellicle formation on the sterile HAP surface. The pellicle coated HAP disc was dip washed and challenged with 30% diluted toothpaste slurry topped up with actives for 2 mins. After 2 min of contact time, the treated HAP was dip washed thrice consecutively in 5 ml of sterile water. The treated HAP discs were challenged with salivary flora and incubated anaerobically at 37° C. for 22-24 h.

At the end 22-24 h incubation, the disc was dip washed thrice in of sterile distilled water. The rinsed disc was immersed in plaque disclosing solution (Plak-Check containing erythrosin, from Vishal Dentocare Pvt Ltd) for 5 min. At the end of 5 min, the stained disc was dip washed thrice consecutively in 5 ml of sterile distilled water. The stained discs were dried at 25±3° C. for 1 hour. Once dried the stain on the discs was eluted using 1 ml of 0.1N NaOH. The absorbance of eluted solution was read at OD540 nm. Higher the absorbance reading, more the formed biofilm on the disc. The results are described in table 1 below.

TABLE 2

|  | % Biofilm |
|---|---|
| Toothpaste base | 100 |
| 0.5% CPC-Clay | 89 |
| 1.5% CPC-Clay | 84 |
| Pluronic 2% | 64 |
| 2% pluronic + 1.5% CPC-Clay | 28 |

The invention claimed is:

1. An antimicrobial composition comprising:
a) a modified clay particle comprising an antimicrobial compound, the modified clay particle comprising:
(i) an asymmetric 1:1 or 2:1:1 clay particle comprising alternating tetrahedral and octahedral sheets terminating with a tetrahedral sheet at one external surface plane and an octahedral sheet at another external surface plane, and
(ii) at least one orally acceptable antimicrobial compound selected from a quaternary ammonium material selected from cetylpyridinium chloride (CPC), cetyltrimethylammonium chloride (CTAC), cetyltrimethylammonium bromide (CTAB), benzalkonium chloride (BKC), benzethonium chloride, cetrimide, quaternium, polyhexamethylene BH; antimicrobial alcohols; antimicrobial phenols; antimicrobial organic acids/salts; zinc pyrithione; ketoconazole; piroctone olamine; or combinations thereof, wherein the at least one antimicrobial compound is attached to a coordinating cation on an external surface plane of the clay particle; and
b) a nonionic triblock copolymer,
wherein the at least one antimicrobial compound is a quaternium ammonium material.

2. The composition according to claim 1, wherein the at least one antimicrobial compound is attached to coordinating cations on the external surface of the octahedral surface plane.

3. The composition according to claim 1, wherein clay: antimicrobial ratio is of between 1:0.001 to 1:0.1.

4. The composition according to claim 1, wherein the antimicrobial particle is in the range of 0.01-5% by weight of the composition.

5. The composition according to claim 1, wherein the nonionic triblock copolymer is poloxamer of general formula I:

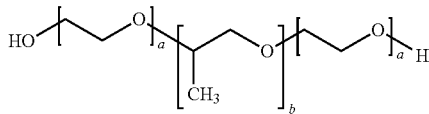

wherein b is an integer such that the hydrophobic base represented by $(C_3H_6O)$ has a molecular weight of about 2750 to 4000, a is an integer such that the hydrophilic portion (moiety) represented by $(C_2H_4O)$ constitutes about 70-80% by weight of the copolymer.

6. The composition according to claim 5, wherein the nonionic triblock copolymer is a poloxamer of general formula I wherein a is 101 and b is 56.

7. The composition according to claim 1, wherein the amount of nonionic triblock copolymer is in the range of 0.01 to 10% by weight of the composition.

8. The composition according to claim 1, wherein the composition further comprises 1 to 80%, by total weight of the composition, of a surfactant.

9. The composition according to claim 1, wherein the composition comprises one or more pharmaceutically acceptable component.

10. The composition according to claim 1, wherein the composition is included in an oral care product selected from toothpaste, dentifrice, tooth powder, topical oral gel, mouth rinse, denture product, mouth spray, lozenge, oral tablet, chewing gum, impregnated dental implement, dental floss, and combinations thereof.

11. An antimicrobial composition, according to claim 1, for use in the prevention or treatment of a disease of a mammal.

12. An antimicrobial composition, according to claim 1, for use in the removal of oral biofilm in a mammal subject.

13. A non-therapeutic method of treating the skin and/or oral cavity of a mammal, the method including the step of contacting the skin and/or oral cavity of a mammal with the antimicrobial composition according to claim 1.

14. An antimicrobial composition, according to claim 1, for use in the prevention or treatment of a disease in the oral cavity selected from the group comprising caries, tartar, dental plaque, gum diseases, and combinations thereof.

* * * * *